United States Patent
McGowan et al.

(10) Patent No.: US 10,499,820 B2
(45) Date of Patent: Dec. 10, 2019

(54) PRESSURE SENSING GUIDEWIRE SYSTEMS INCLUDING AN OPTICAL CONNECTOR CABLE

(71) Applicant: BOSTON SCIENTIFIC SCIMED, INC., Maple Grove, MN (US)

(72) Inventors: Roger W. McGowan, Otsego, MN (US); Christopher Smuk, Champlin, MN (US); Peter Thornton, Jr., Los Altos, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2 days.

(21) Appl. No.: 14/285,344

(22) Filed: May 22, 2014

(65) Prior Publication Data

US 2014/0350414 A1  Nov. 27, 2014

Related U.S. Application Data

(60) Provisional application No. 61/826,412, filed on May 22, 2013.

(51) Int. Cl.
| | |
|---|---|
| *A61B 5/02* | (2006.01) |
| *A61B 5/0215* | (2006.01) |
| *A61B 5/026* | (2006.01) |
| *A61B 5/00* | (2006.01) |
| *G02B 6/36* | (2006.01) |

(52) U.S. Cl.
CPC .......... *A61B 5/02154* (2013.01); *A61B 5/026* (2013.01); *A61B 5/02007* (2013.01); *A61B 5/02158* (2013.01); *A61B 5/6851* (2013.01); *G02B 6/3604* (2013.01); *A61B 2562/228* (2013.01)

(58) Field of Classification Search
None
See application file for complete search history.

(56) References Cited

U.S. PATENT DOCUMENTS

| | | |
|---|---|---|
| 3,963,323 A | 6/1976 | Arnold |
| 4,771,782 A | 9/1988 | Millar |
| 4,953,553 A | 9/1990 | Tremulis |
| 5,106,455 A | 4/1992 | Jacobsen et al. |

(Continued)

FOREIGN PATENT DOCUMENTS

| | | |
|---|---|---|
| DE | 202014100938 U1 | 3/2014 |
| EP | 0235992 A1 | 9/1987 |

(Continued)

*Primary Examiner* — Joel F Brutus
(74) *Attorney, Agent, or Firm* — Seager, Tufte & Wickhem, LLP

(57) ABSTRACT

Medical devices and methods for making and using medical devices are disclosed. An example medical device may include a system for measuring blood pressure. The system may include a pressure sensing guidewire including a pressure sensor and a first optical fiber extending proximally from the pressure sensor. The system may also include an optical connector cable including a distal connector capable of being coupled to the guidewire. The optical connector cable may include a second optical fiber that is capable of optically communicating with the first optical fiber. A coupler may be disposed within the distal connector and disposed between the first optical fiber and the second optical fiber.

11 Claims, 10 Drawing Sheets

(56) References Cited

U.S. PATENT DOCUMENTS

| | | |
|---|---|---|
| 5,178,159 A | 1/1993 | Christian |
| 5,238,004 A | 8/1993 | Sahatjian et al. |
| 5,313,957 A | 5/1994 | Little |
| 5,322,064 A * | 6/1994 | Lundquist .......... A61B 18/1492 600/381 |
| 5,414,507 A * | 5/1995 | Herman .............. G01L 9/0039 250/227.21 |
| 5,421,195 A | 6/1995 | Wlodarczyk |
| 5,422,969 A | 6/1995 | Eno |
| 5,427,114 A | 6/1995 | Colliver et al. |
| 5,438,873 A | 8/1995 | Wlodarczyk et al. |
| 5,573,520 A | 11/1996 | Schwartz et al. |
| 5,633,963 A | 5/1997 | Rickenbach et al. |
| 5,755,668 A | 5/1998 | Itoigawa et al. |
| 5,772,609 A | 6/1998 | Nguyen et al. |
| 5,797,856 A | 8/1998 | Frisbie et al. |
| 5,872,879 A | 2/1999 | Hamm |
| 5,902,248 A | 5/1999 | Millar et al. |
| 5,938,624 A | 8/1999 | Akerfeldt et al. |
| 5,949,929 A | 9/1999 | Hamm |
| 6,112,598 A | 9/2000 | Tenerz et al. |
| 6,120,457 A | 9/2000 | Coombes et al. |
| 6,139,510 A | 10/2000 | Palmero |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,508,803 B1 | 1/2003 | Horikawa et al. |
| 6,565,514 B2 | 5/2003 | Svanerudh et al. |
| 6,579,246 B2 | 6/2003 | Jacobsen et al. |
| 6,579,484 B1 * | 6/2003 | Tiernan ............. A61M 25/0009 264/173.16 |
| 6,585,660 B2 | 7/2003 | Dorando et al. |
| 6,589,164 B1 * | 7/2003 | Flaherty ............ A61M 25/0017 600/121 |
| 6,615,067 B2 | 9/2003 | Hoek et al. |
| 6,663,570 B2 | 12/2003 | Mott et al. |
| 6,702,478 B2 | 3/2004 | Inagaki et al. |
| 6,766,720 B1 | 7/2004 | Jacobsen et al. |
| 6,767,327 B1 | 7/2004 | Cori et al. |
| 6,776,720 B2 | 8/2004 | Bartlett |
| 6,908,442 B2 | 6/2005 | Von Malmborg et al. |
| 6,918,882 B2 | 6/2005 | Skujins et al. |
| 6,918,873 B1 | 7/2005 | Millar et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,259,862 B2 | 8/2007 | Duplain et al. |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 | 8/2010 | Ainsworth et al. |
| 7,878,984 B2 | 2/2011 | Davis et al. |
| 7,930,014 B2 | 4/2011 | Huenneckens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 | 1/2013 | Sela et al. |
| 8,410,940 B2 | 4/2013 | Samuelsson et al. |
| 8,461,997 B2 | 6/2013 | Samuelsson et al. |
| 8,485,985 B2 | 7/2013 | Manstrom et al. |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,936,401 B2 | 1/2015 | Belleville et al. |
| 8,998,823 B2 | 4/2015 | Manstrom et al. |
| 9,052,466 B2 | 6/2015 | Belleville et al. |
| 2003/0031422 A1 * | 2/2003 | Inagaki ............... G02B 6/3825 385/72 |
| 2003/0069522 A1 | 4/2003 | Jacobsen et al. |
| 2004/0073141 A1 | 4/2004 | Hartley et al. |
| 2004/0181174 A2 | 9/2004 | Davis et al. |
| 2004/0258370 A1 * | 12/2004 | Bush ................... G02B 6/2551 385/97 |
| 2005/0000294 A1 | 1/2005 | Tenerz et al. |
| 2006/0122537 A1 | 6/2006 | Reynolds et al. |
| 2008/0119758 A1 | 5/2008 | Samuelsson et al. |
| 2008/0285909 A1 * | 11/2008 | Younge ............... A61B 5/1076 385/13 |
| 2009/0082678 A1 | 3/2009 | Smith |
| 2009/0116020 A1 * | 5/2009 | Wu .................. G01N 33/54373 356/445 |
| 2009/0192412 A1 | 7/2009 | Sela et al. |
| 2010/0087605 A1 * | 4/2010 | Yamamoto ........... C08F 220/14 526/64 |
| 2010/0145308 A1 | 6/2010 | Layman et al. |
| 2010/0241008 A1 | 9/2010 | Belleville et al. |
| 2011/0071407 A1 | 3/2011 | Hübinette et al. |
| 2011/0178413 A1 | 7/2011 | Schmitt et al. |
| 2011/0186294 A1 | 8/2011 | Narvaez et al. |
| 2011/0319773 A1 | 12/2011 | Kanz et al. |
| 2012/0083794 A1 * | 4/2012 | Martin ................ A61B 17/3415 606/108 |
| 2012/0227505 A1 | 9/2012 | Belleville et al. |
| 2012/0265102 A1 | 10/2012 | Leo et al. |
| 2013/0051731 A1 * | 2/2013 | Belleville ............ G02B 6/3861 385/72 |
| 2013/0218032 A1 | 8/2013 | Belleville |
| 2013/0296718 A1 * | 11/2013 | Ranganathan .......... A61B 5/02 600/481 |
| 2013/0317372 A1 | 11/2013 | Eberle et al. |
| 2014/0005558 A1 | 1/2014 | Gregorich |
| 2014/0058275 A1 | 2/2014 | Gregorich et al. |
| 2014/0081244 A1 | 3/2014 | Voeller et al. |
| 2014/0107624 A1 | 4/2014 | Belleville |
| 2014/0121475 A1 | 5/2014 | Alpert et al. |
| 2014/0241669 A1 | 8/2014 | Belleville et al. |
| 2014/0248021 A1 | 9/2014 | Belleville et al. |

FOREIGN PATENT DOCUMENTS

| | | |
|---|---|---|
| EP | 0738495 A1 | 10/1996 |
| EP | 0879615 A1 | 11/1998 |
| EP | 0879617 A1 | 11/1998 |
| EP | 1479407 A1 | 11/2004 |
| JP | 213919 A | 1/1990 |
| JP | H11-1258476 A | 9/1999 |
| JP | 2001507251 A | 6/2001 |
| JP | 2008101203 A | 5/2008 |
| JP | 4573233 B2 | 11/2010 |
| JP | 201275890 A | 4/2012 |
| WO | 9313707 A1 | 7/1993 |
| WO | 9533983 A1 | 12/1995 |
| WO | 9823984 A2 | 6/1998 |

(56) References Cited

FOREIGN PATENT DOCUMENTS

| | | | |
|---|---|---|---|
| WO | 9945352 | A1 | 9/1999 |
| WO | 2008034010 | A2 | 3/2008 |
| WO | 2011027282 | A1 | 3/2011 |
| WO | 2011090744 | A2 | 7/2011 |
| WO | 2011123689 | A1 | 10/2011 |
| WO | 2012000798 | A1 | 1/2012 |
| WO | 2012090210 | A1 | 7/2012 |
| WO | 2013029157 | A1 | 3/2013 |
| WO | 2013033489 | A1 | 3/2013 |
| WO | 2014025255 | A1 | 2/2014 |

\* cited by examiner

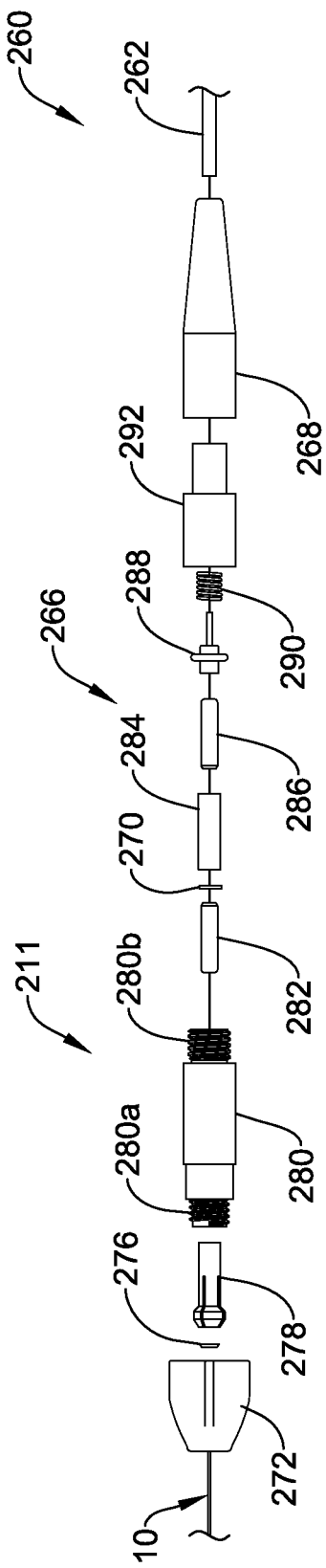
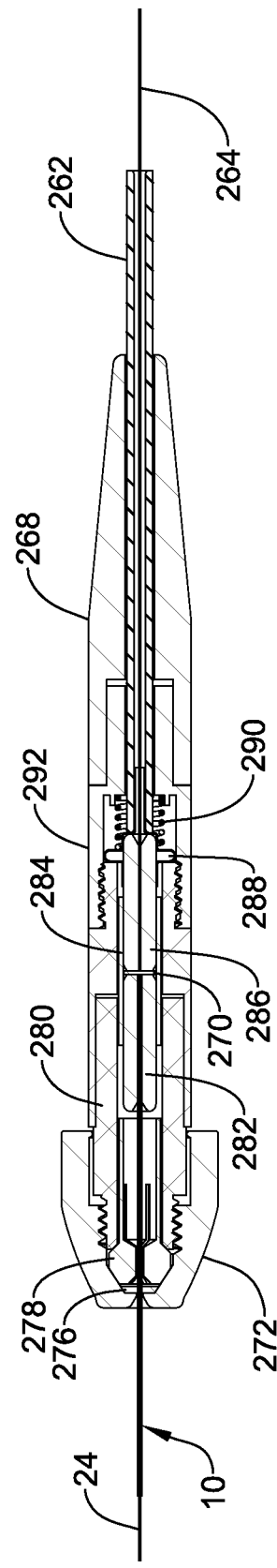
Figure 6
Figure 7

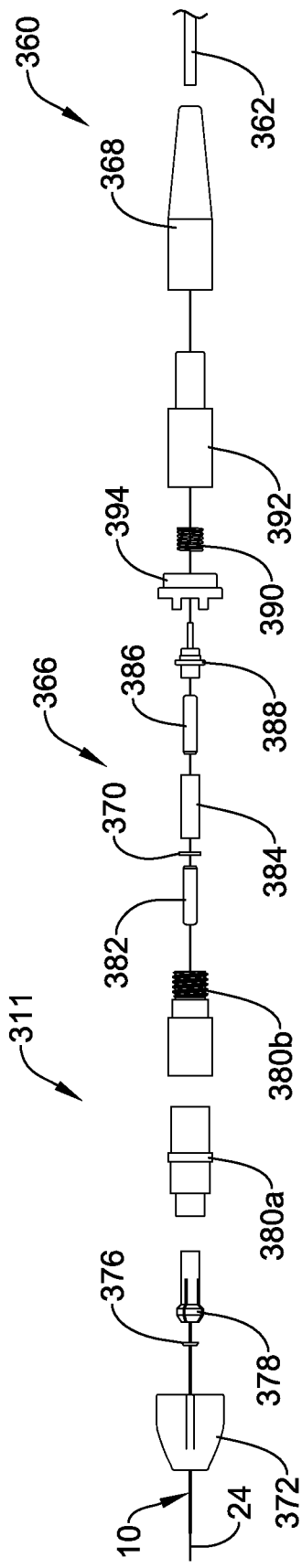
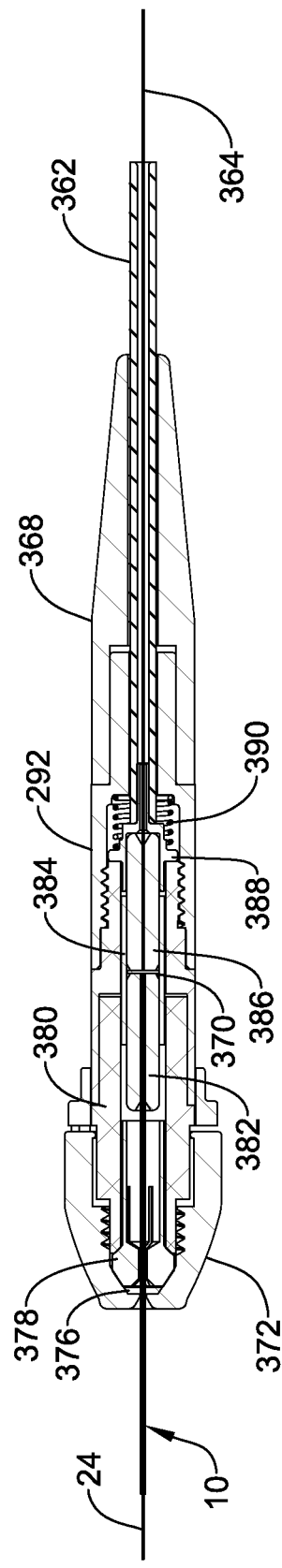
Figure 8
Figure 9

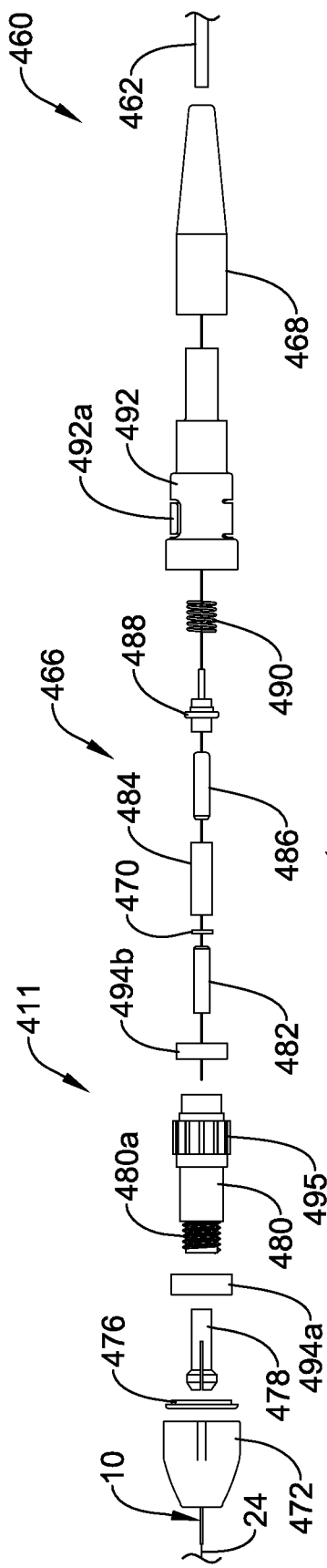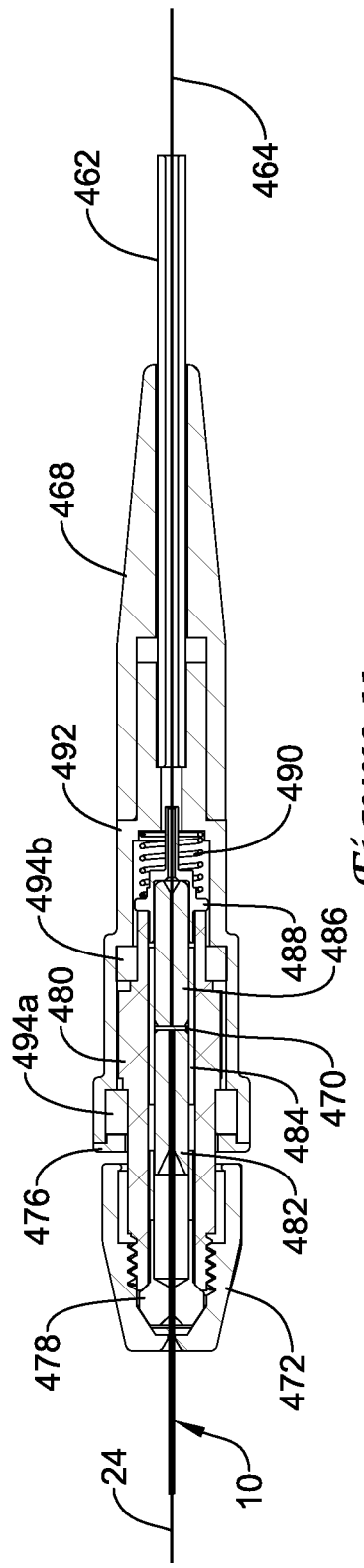
Figure 10
Figure 11

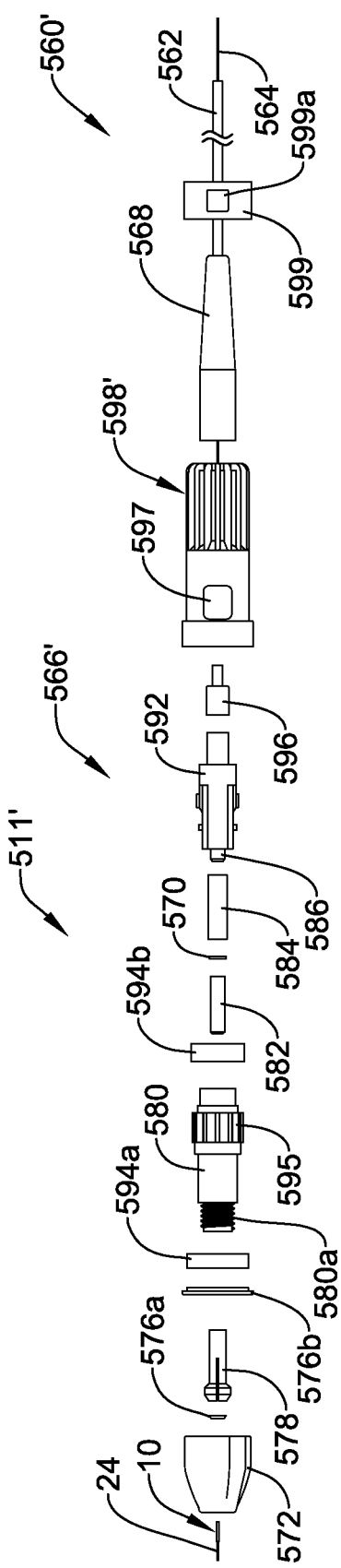
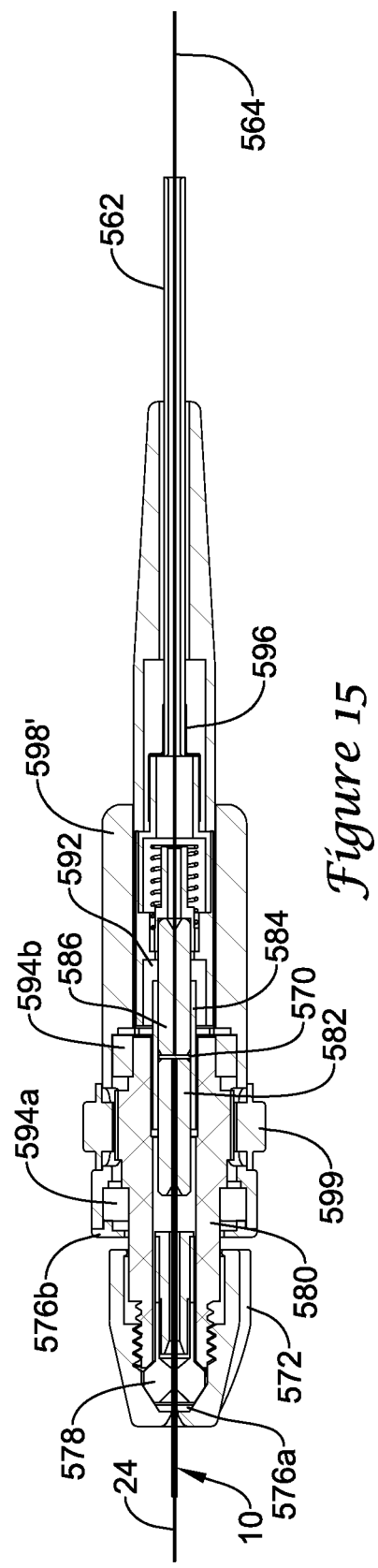
Figure 14
Figure 15

PRESSURE SENSING GUIDEWIRE SYSTEMS INCLUDING AN OPTICAL CONNECTOR CABLE

CROSS-REFERENCE TO RELATED APPLICATIONS

This application claims priority under 35 U.S.C. § 119 to U.S. Provisional Application Ser. No. 61/826,412, filed May 22, 2013, the entirety of which is incorporated herein by reference.

TECHNICAL FIELD

The present disclosure pertains to medical devices, and methods for manufacturing medical devices. More particularly, the present disclosure pertains to blood pressure sensing guidewires and methods for using pressure sensing guidewires.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device may include a system for measuring blood pressure. The system may include a pressure sensing guidewire including a pressure sensor and a first optical fiber extending proximally from the pressure sensor. The system may also include an optical connector cable including a distal connector capable of being coupled to the guidewire. The optical connector cable may include a second optical fiber that is capable of optically communicating with the first optical fiber. A coupler may be disposed within the distal connector and disposed between the first optical fiber and the second optical fiber.

Other example systems may include systems for determining fractional flow reserve. Such systems may include a pressure sensing guidewire including an optical pressure sensor and a first optical fiber extending proximally from the optical pressure sensor. The system may also include an optical connector cable including a distal connector capable of being coupled to the guidewire. In some embodiments, distal connector is a rotatable connector capable of being rotatably coupled to the guidewire. The optical connector cable may include a second optical fiber that is capable of optically communicating with the first optical fiber. A coupler may be disposed within the distal connector and disposed between the first optical fiber and the second optical fiber.

Another example system for determining fractional flow reserve may include a pressure sensing guidewire including an optical pressure sensor and a first optical fiber extending proximally from the optical pressure sensor. The first optical fiber may have a first index of refraction. The system may include an optical connector cable including a rotatable distal connector capable of being rotatably coupled to the guidewire. The optical connector cable may include a second optical fiber that is capable of optically communicating with the first optical fiber. The second optical fiber may have a second index of refraction. A coupler may be disposed within the rotatable distal connector and disposed between the first optical fiber and the second optical fiber. The coupler may have a third index of refraction that is substantially the same as the first index of refraction, the second index of refraction, or both.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 6 is an exploded view of a portion of another example medical device system;

FIG. 7 is a partial cross-sectional side view of the example medical device system shown in FIG. 6;

FIG. 8 is an exploded view of a portion of another example medical device system;

FIG. 9 is a partial cross-sectional side view of the example medical device system shown in FIG. 8;

FIG. 10 is an exploded view of a portion of another example medical device system;

FIG. 11 is a partial cross-sectional side view of the example medical device system shown in FIG. 10;

FIG. 14 is an exploded view of a portion of another example medical device system; and FIG. 15 is a partial cross-sectional side view of the example medical device system shown in FIG. 14.

Figure 1:
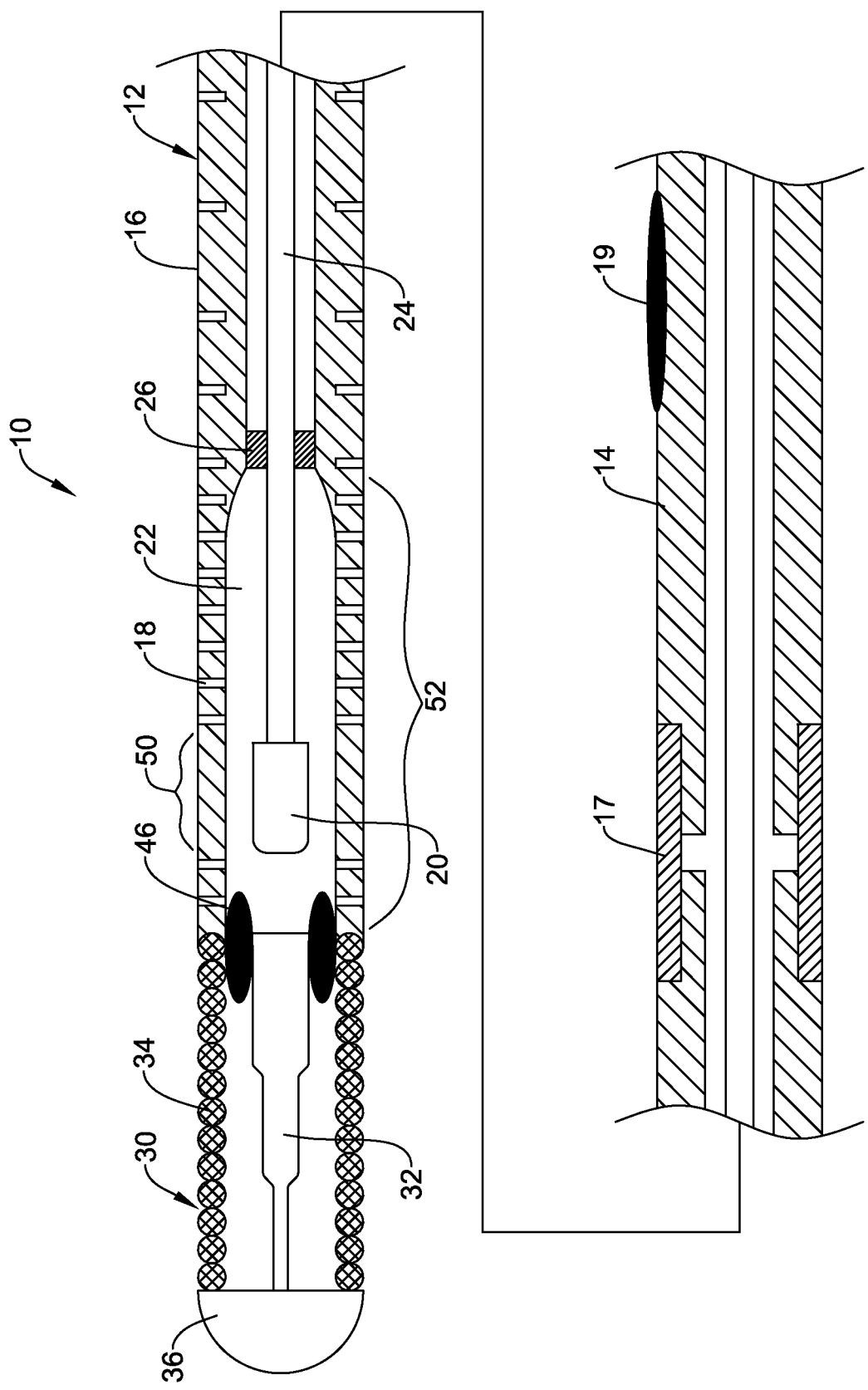
FIG. 1 is a partial cross-sectional side view of a portion of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis (and/or the aortic pressure).

FIG. 1 illustrates a portion of an example medical device 10. In this example, medical device 10 is a blood pressure sensing guidewire 10. However, this is not intended to be limiting as other medical devices are contemplated including, for example, catheters, shafts, leads, wires, or the like. Guidewire 10 may include a guidewire shaft or tubular member 12. Tubular member 12 may include a proximal portion 14 and a distal portion 16. The materials for proximal portion 14 and distal portion 16 may vary and may include those materials disclosed herein. For example, distal portion 16 may include a nickel-cobalt-chromium-molybdenum alloy (e.g., MP35-N). Proximal portion 14 may include stainless steel. These are just examples. Other materials may also be utilized.

In some embodiments, proximal portion 14 and distal portion 16 are formed from the same monolith of material. In other words, proximal portion 14 and distal portion 16 are portions of the same tube defining tubular member 12. In other embodiments, proximal portion 14 and distal portion 16 are separate tubular members that are joined together. For example, a section of the outer surface of portions 14/16 may be removed and a sleeve 17 may be disposed over the removed sections to join portions 14/16. Alternatively, sleeve 17 may be simply disposed over portions 14/16. Other bonds may also be used including welds, thermal bonds, adhesive bonds, or the like. If utilized, sleeve 17 used to join proximal portion 14 with distal portion 16 may include a material that desirably bonds with both proximal portion 14 and distal portion 16. For example, sleeve 17 may include a nickel-chromium-molybdenum alloy (e.g., INCONEL).

A plurality of slots 18 may be formed in tubular member 12. In at least some embodiments, slots 18 are formed in distal portion 16. In at least some embodiments, proximal portion 14 lacks slots 18. However, proximal portion 14 may include slots 18. Slots 18 may be desirable for a number of reasons. For example, slots 18 may provide a desirable level of flexibility to tubular member 12 (e.g., along distal portion 16) while also allowing suitable transmission of torque. Slots 18 may be arranged/distributed along distal portion 16 in a suitable manner including any of those arrangements disclosed herein. For example, slots 18 may be arranged as opposing pairs of slots 18 that are distributed along the length of distal portion 16. In some embodiments, adjacent pairs of slots 18 may have a substantially constant spacing relative to one another. Alternatively, the spacing between adjacent pairs may vary. For example, more distal regions of distal portion 16 may have a decreased spacing (and/or increased slot density), which may provide increased flexibility. In other embodiments, more distal regions of distal portion 16 may have an increased spacing (and/or decreased slot density). These are just examples. Other arrangements are contemplated.

A pressure sensor 20 may be disposed within tubular member 12 (e.g., within a lumen 22 of tubular member 12). While pressure sensor 20 is shown schematically in FIG. 1, it can be appreciated that the structural form and/or type of pressure sensor 20 may vary. For example, pressure sensor 20 may include a semiconductor (e.g., silicon wafer) pressure sensor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, pressure sensor 20 may include an optical pressure sensor. In at least some of these embodiments, a fiber optic cable 24 may be attached to pressure sensor 20 and may extend proximally therefrom. An attachment member 26 may attach fiber optic cable 24 to tubular member 12. Attachment member 26 may be circumferentially disposed about and attached to optical fiber 24 and may be secured to the inner surface of tubular member 12 (e.g., distal portion 16). In at least some embodiments, attachment member 26 is proximally spaced from pressure sensor 20. Other arrangements are contemplated.

In at least some embodiments, distal portion 16 may include a region with a thinned wall and/or an increased inner diameter that defines a housing region 52. In general, housing region 52 is the region of distal portion 16 that ultimately "houses" the pressure sensor (e.g., pressure sensor 20). By virtue of having a portion of the inner wall of tubular member 12 being removed at housing region 52, additional space may be created or otherwise defined that can accommodate sensor 20.

In at least some embodiments, it may be desirable for pressure sensor 20 to have reduced exposure along its side surfaces to fluid pressure (e.g., from the blood). Accordingly, it may be desirable to position pressure sensor 20 along a landing region 50 defined along housing region 52. Landing region 50 may be substantially free of slots 18 so that the side surfaces of pressure sensor 20 have a reduced likelihood of being deformed due to fluid pressures at these locations.

Distal of landing are 50, housing region 52 may include slots 18 that provide fluid access to pressure sensor 20.

Moreover, slots 18 may define a fluid pathway that allows blood (and/or a body fluid) to flow from a position along the exterior or outer surface of guidewire 10 (and/or tubular member 12), through slots 18, and into the lumen 22 of tubular member 12, where the blood can come into contact with pressure sensor 20. Because of this, no additional side openings/holes (e.g., other than slots 18) may be necessary in tubular member 12 for pressure measurement. This may also allow the length of distal portion 16 to be shorter than typical sensor mounts or hypotubes that would need to have a length sufficient for a suitable opening/hole (e.g., a suitable "large" opening/hole) to be formed therein that provides fluid access to sensor 20.

A tip member 30 may be coupled to distal portion 16. Tip member 30 may include a shaping member 32 and a spring or coil member 34. A distal tip 36 may be attached to shaping member 32 and/or spring 34. In at least some embodiments, distal tip 36 may take the form of a solder ball tip. Tip member 30 may be joined to distal portion 16 of tubular member 12 with a bonding member 46 such as a weld.

Tubular member 12 may include a hydrophilic coating 19. In some embodiments, hydrophilic coating 19 may extend along substantially the full length of tubular member 12. In other embodiments, one or more discrete sections of tubular member 12 may include hydrophilic coating 19.

Figure 2:
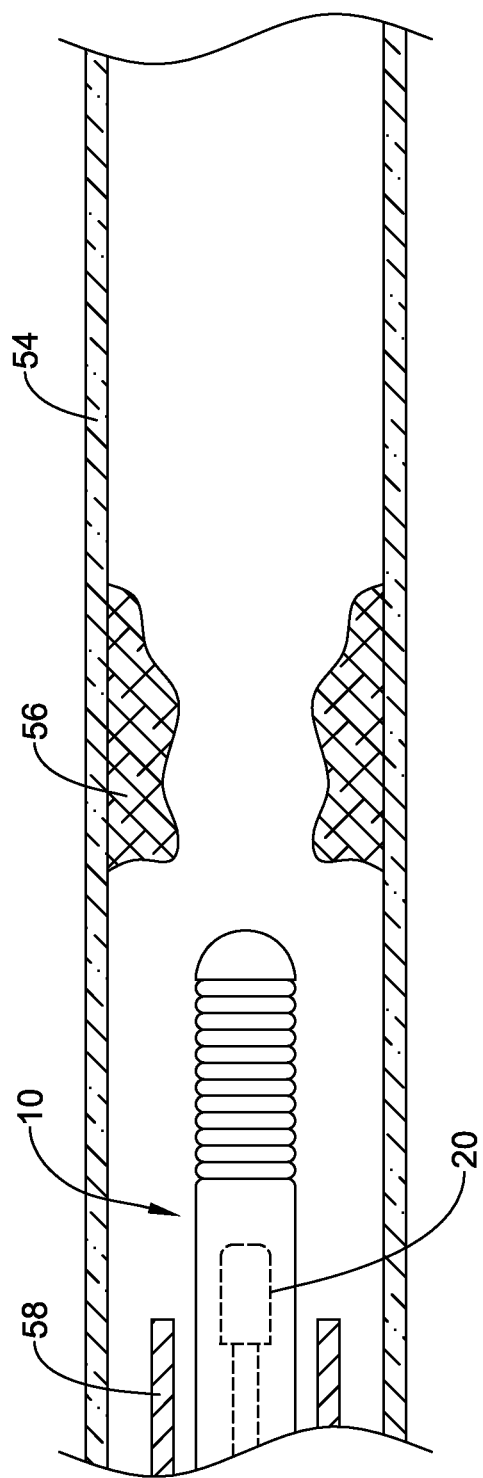
FIG. 2 is a partial cross-sectional view of an example medical device disposed at a first position adjacent to an intravascular occlusion.
Figure 3:
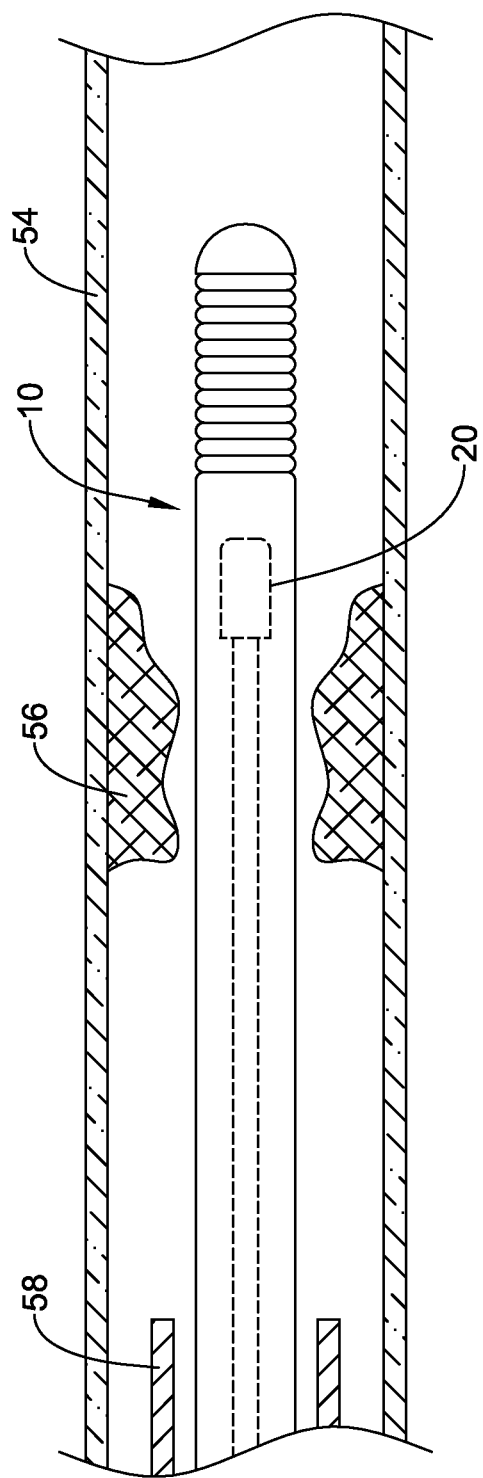
FIG. 3 is a partial cross-sectional view of an example medical device disposed at a second position adjacent to an intravascular occlusion.

In use, a clinician may use guidewire 10 to measure and/or calculate FFR (e.g., the pressure after an intravascular occlusion relative to the pressure before the occlusion and/or the aortic pressure). Measuring and/or calculating FFR may include measuring the aortic pressure in a patient. This may include advancing guidewire 10 through a blood vessel or body lumen 54 to a position that is proximal or upstream of an occlusion 56 as shown in FIG. 2. For example, guidewire 10 may be advanced through a guide catheter 58 to a position where at least a portion of sensor 20 is disposed distal of the distal end of guide catheter 58 and measuring the pressure within body lumen 54. This pressure may be characterized as an initial pressure. In some embodiments, the aortic pressure may also be measured by another device (e.g., a pressure sensing guidewire, catheter, or the like). The initial pressure may be equalized with the aortic pressure. For example, the initial pressure measured by guidewire 10 may be set to be the same as the measured aortic pressure. Guidewire 10 may be further advanced to a position distal or downstream of occlusion 56 as shown in FIG. 3 and the pressure within body lumen 54 may be measured. This pressure may be characterized as the downstream or distal pressure. The distal pressure and the aortic pressure may be used to calculate FFR.

It can be appreciated that an FFR system that utilizes an optical pressure sensor in a pressure sensing guidewire may be connected to a number of processing/conditioning units, displays, and the like. When making these connections, the various cables/connections may be designed so that the optical signals can be transmitted between adjacent optical fibers in an efficient manner.

A wide variety of optical connectors exist that are designed to allow for efficient communication between adjacent optical fibers. Such connectors are typically utilized in industries such as telecommunication. The use of optical fibers in medical devices provides a variety of new challenges. When optical fibers are utilized in medical devices, the connectors may need to allow for the connection of various devices and/or components while allowing for movement (e.g., rotation) of the components relative to one another during use. These movements could lead to complications. For example, the polished end surfaces of the fiber could contact one another, which could ultimately scratch, rub, or damage the fibers. This could impact the optical communication between the fibers. At least some of the medical devices, medical device systems, and connectors disclosed herein may include features that improve the connection of components of a fiber optic system such as the connection of optical fibers.

For the purposes of this disclosure, reference will be made to "medical device systems". The medical device systems may be understood to be one or more medical devices that may be used together. In at least some embodiments, the medical device systems disclosed herein may be systems for measuring FFR. These systems may include a pressure sensing guidewire, an optical connector cable coupled to the guidewire, a signal conditioning unit and/or processing unit coupled to the optical connector cable, and a display unit or output. The systems may also include additional intermediate cables and/or devices, guide catheters, other pressure measuring devices and/or components, and the like. References made to a system are not meant to imply that all of these components are present.

Figure 4:
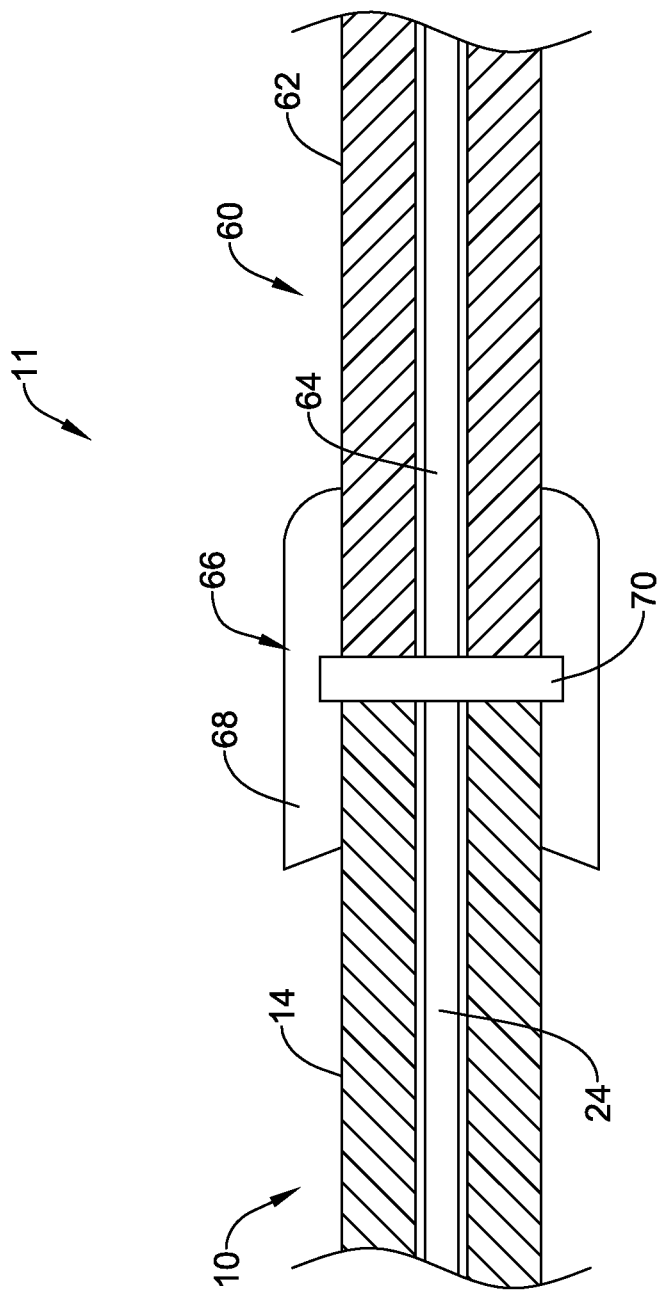
FIG. 4 is a partial cross-sectional side view of a portion of an example medical device system.

FIG. 4 schematically illustrates a portion of an example medical device system 11. Here it can be seen that proximal portion 14 of guidewire 10 may be coupled to an example optical connector cable 60. Connector cable 60 may include a cable body 62, an optical fiber 64, and a distal connector 66. Distal connector 66 may include a connector housing 68. Connector cable 60 may be utilized to optically connect optical fiber 24 with fiber 64, which extends to one or more components of system 11 including, for example, a signal conditioning unit.

As suggested above, movement and/or contact between adjacent optical fibers such as fibers 24/64 could lead to damage of the polished ends of the fibers 24/64. This could impact the communication between fibers 24/64. In order to improve the communication between fibers 24/64, a coupler 70 may be disposed within distal connector 66. Coupler 70 may be disposed between the ends of fibers 24/64. In at least some embodiments, coupler 70 may be a deformable disc or cylinder. For example, coupler 70 may take the form of a polymer disc. This may include a disc or cylinder formed from a compliant material such as an optically clear (e.g., aliphatic) polyurethane. Other forms are also contemplated for coupler 70. For example, coupler 70 may be a gel (e.g., a relatively thick gel), a coating on one or both of fibers 26/64, a membrane, or the like. Coupler 70 may be formed from one or more polymers or from other suitable materials including those disclosed herein. In at least some embodiments, coupler 70 may function as a "cushioning member" or a structural feature that provides some level deformability at the interface between fibers 24/64 when bringing together fibers 24/64 (and/or bringing together guidewire 10 and optical connector cable 60).

The proximal end of guidewire 10 may be advanced into distal connector 66 until optical fiber 24 (and the proximal end of guidewire 10) presses against coupler 70. This may help to reduce or eliminate any air and/or fluids that could be present between the ends of fibers 24/64, which could otherwise impact the transmission of light between fibers 24/64. In addition, coupler 70 may help to soften any contact between the ends of fibers 24/64 that could otherwise scratch, rub, or damage the ends of fibers 24/64. In addition, distal connector 66 may be manufactured to have a larger space for guidewire 10 to fit into due to coupler 70 having the ability to deform or "give" when contacting guidewire 10. Coupler 70 may also function as an optical bearing that allows guidewire 10 to be rotated with little frictional forces. In addition, coupler 70 may be formed from a material that sheds fluids, which may help make distal connector 66 act as a "self-cleaning" connector.

Coupler 70 may be transparent so that light may essentially pass freely from fiber 24 to fiber 64. In at least some embodiment, coupler 70 may have an index of refraction that approximate the index of refraction of optical fiber 24, optical fiber 64, or both. In other words, coupler 70 may be index matched with fibers 24/64. This may be desirable for a number of reasons. For example, reflective losses between fibers 24/64 may be reduced. In addition, signal noise that may be present within distal connector 66 may also be reduced. In at least some embodiments, coupler 70 may have a thickness on the order of about 25 to 400 microns, or about 100 to 200 microns. In general, these sizes may have negligible signal losses. Smaller sizes for coupler 70 may also be utilized in some embodiments, for example, where coupler 70 takes the form of a coating. These are just examples. Other features, dimensions, properties may also be present.

Figure 5:
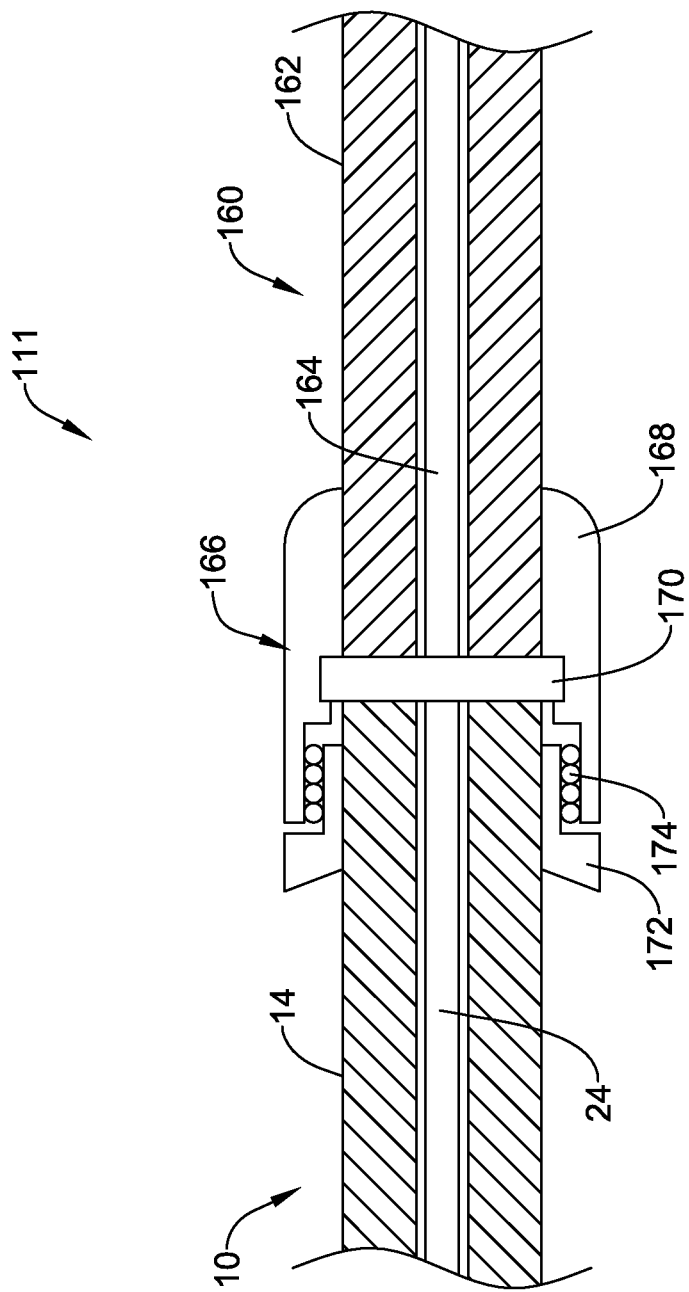
FIG. 5 is a partial cross-sectional side view of a portion of another example medical device system.

FIG. 5 schematically illustrates a portion of another example medical device system 111 that may be similar in form and function to other systems disclosed herein. Here it can be seen that proximal portion 14 of guidewire 10 may be coupled to another example optical connector cable 160 including cable body 162 and optical fiber 164. Connector cable 160 may include distal connector 166. Coupler 170 may be disposed within distal connector 166 and may function similarly to coupler 70.

Distal connector 166 may be a rotatable connector that allows guidewire 10 to be rotated relative to connector cable 160. Distal connector 166 may include housing 168, rotatable member 172, and one or more bearings 174. Rotatable member 172 may be secured to guidewire 10 and can rotate relative to housing 168. The use of coupler 170 may be desirable for reasons indicated above. In addition, coupler 170 may help to reduce fiber damage and/or signal disruption at the rotatable connection.

FIGS. 6-7 illustrate a portion of example medical device system 211 that may be similar in form and function to other systems disclosed herein. System 211 may include optical connector cable 260 with cable body 262 and distal connector 266. Guidewire 10 may be coupled to optical connector cable 260. Distal connector 266 may include a body 280 with threaded ends 280a/280b. A collet 278 may be disposed within body 280. A collet nut 272 may be coupled to body 280, for example at end 280a. Connector 266 may also include proximal body 268, housing 292, a spring 290, and a flanged body 288 that is secured (e.g., via an adhesive bond or other suitable bond) to a ferrule 286.

The structural components of distal connector 266 and/or other connectors disclosed herein may vary. For example, while FIGS. 6-7 illustrate collet 278 for securing guidewire 10, other structures may be utilized. For example, another structure such as spring loaded jaws, an assembly with rollers and a clutch to secure guidewire 10, or other structural features may be utilized. In addition, in at least some embodiments, body 268 may be a strain relief. In some of these and in other embodiments, body 268 may include a wire that allows body 268 to be bent into another shape (e.g., a curved shape) and retain that shape. Other variations are also contemplated for distal connector 266 and/or other connectors disclosed herein.

In use, guidewire 10 may extend through collet nut 272, through a retaining ring 276, through collet 278, through body 280, and into a ferrule 282. Ferrule 282 may extend into a split sleeve 284. Tightening collet nut 272 onto body 280 may press collet 278 onto guidewire 10 and secure guidewire 10. Tightening collet nut 272 may move or press guidewire 10 into coupler 270. Cable body 262 may include optical fiber 264, which extends through body 268, through spring 290, through flanged body 288, and into ferrule 286 (and secured thereto using a suitable bond such as an adhesive bond). Ferrule 286 may extend into split sleeve 284 so that fiber 264 can be positioned adjacent to fiber 24. Split sleeve 284 may have a slit formed therein that allows split sleeve 284 to expand when ferrules 282/286 are disposed therein. Coupler 270 may be disposed within split sleeve 284 at a position between optical fiber 24 (of guidewire 10) and optical fiber 264. Coupler 270 may be similar in form and function to other couplers disclosed herein.

FIGS. 8-9 illustrate a portion of example medical device system 311 that may be similar in form and function to other systems disclosed herein. System 311 may include optical connector cable 360 with cable body 362 and distal connector 366. Guidewire 10 may be coupled to optical connector cable 360. Distal connector 366 may include body portions 380a/380b. Collet 378 may be disposed within one or more of body portions 380a/380b (e.g., body portion 380a). Collet nut 372 may be coupled to body portions 380a/380b. For example, body portion 380a may include a threaded end (not shown) and collet nut 372 may be threaded thereon. Connector 366 may also include proximal body 368, housing 392, a spring 390, and flanged body 388 that is secured (e.g., via an adhesive bond or other suitable bond) to ferrule 386. Connector 366 may also include a stop nut 394. Stop nut 394 also be disposed within connector 366 that may be capable of engaging body portions 380a/380b and may help to prevent over-tightening of collet nut 372.

In use, guidewire 10 may extend through collet nut 372, through retaining ring 376, through collet 378, through body portions 380a/380b, and into ferrule 382. Ferrule 382 may extend into split sleeve 384. Tightening collet nut 372 onto body 380a may press collet 378 onto guidewire 10 and secure guidewire 10. Cable body 362 may include optical fiber 364, which extends through body 368, through spring 390, through flanged body 388, and into ferrule 386 (and secured thereto using a suitable bond such as an adhesive bond). Ferrule 386 may extend into split sleeve 384 so that fiber 364 can be positioned adjacent to fiber 24. Coupler 370 may be disposed within split sleeve 384 at a position between optical fiber 24 (of guidewire 10) and optical fiber 364. Coupler 370 may be similar in form and function to other couplers disclosed herein.

FIGS. 10-11 illustrate a portion of example medical device system 411 that may be similar in form and function to other systems disclosed herein. System 411 may include optical connector cable 460 with cable body 462 and distal connector 466. Guidewire 10 may be coupled to optical connector cable 460. Distal connector 466 may be a rotatable connector that allows guidewire 10 to rotate relative to optical connector cable 460.

Distal connector 466 may include body 480 (e.g., a rotatable body 480) with threaded end 480a. Body 480 may have one or more projections 495 formed thereon. Collet 478 may be disposed within body 480. Collet nut 472 may be coupled to body 480, for example at end 480a.

In use, guidewire 10 may extend through collet nut 472, through retaining ring 476, through collet 478, through a first bearing 494a, through body 480, through a second bearing 494b, and into ferrule 482. Ferrule 482 may extend into split sleeve 484. Tightening collet nut 472 onto body 480 may press collet 478 onto guidewire 10 and secure guidewire 10. Cable body 462 may include optical fiber 464, which extends through body 468, through housing 492, through spring 490, through flanged body 488, and into ferrule 486 (and secured thereto using a suitable bond such as an adhesive bond). Ferrule 486 may extend into split sleeve 484 so that fiber 464 can be positioned adjacent to fiber 24. Coupler 470 may be disposed within split sleeve 484 at a position between optical fiber 24 (of guidewire 10) and optical fiber 464. Coupler 470 may be similar in form and function to other couplers disclosed herein.

As indicated above, distal connector 466 may be a rotatable connector that allows guidewire 10 to rotate relative to connector cable 460. For example, distal connector 466 may include bearings 494a/494b that allows guidewire 10 to rotate relative connector cable 460. Housing 492 may include one or more projections or tabs 492a (e.g., a deflectable member 492a). Tabs 492a may be depressed or otherwise deformed so as to grip projections 495 on body 480. Gripping projections 495 on body 480 may allow collet nut 472 to be secured to body 480. Other structures may also be utilized to secure body 480 while tightening collet nut 472 such as a locking ring, lever, or the like. In addition a stop (similar to stop nut 394) may also be included.

Figure 12:
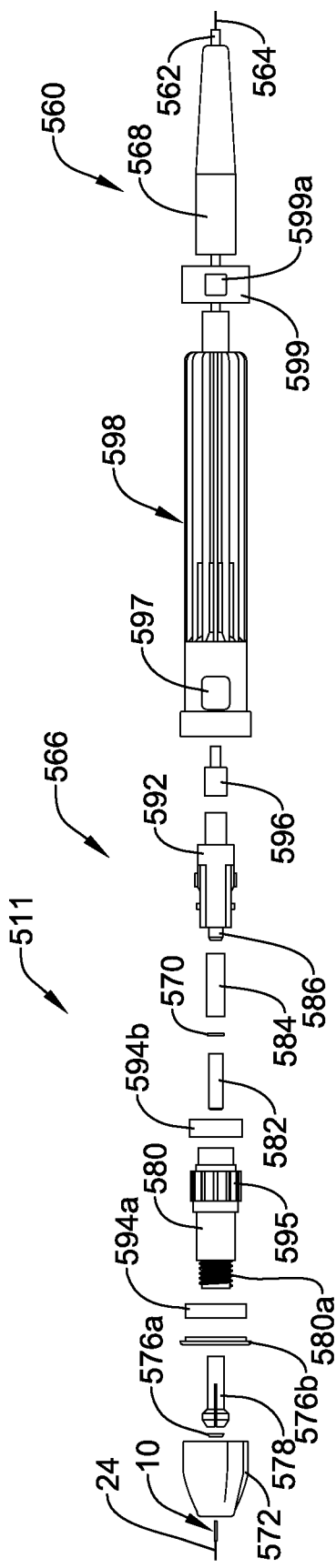
FIG. 12 is an exploded view of a portion of another example medical device system.
Figure 13:
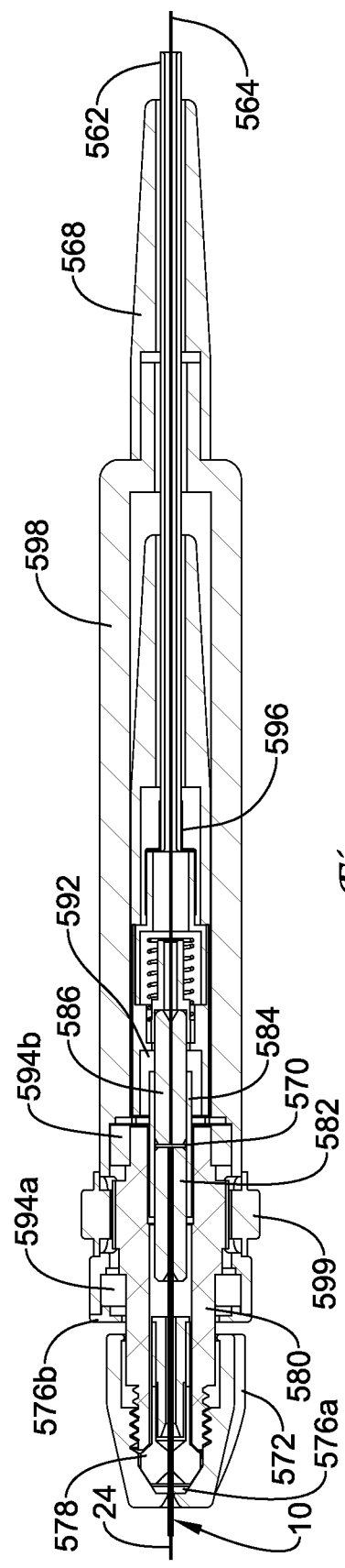
FIG. 13 is a partial cross-sectional side view of the example medical device system shown in FIG. 12.

FIGS. 12-13 illustrate a portion of example medical device system 511 that may be similar in form and function to other systems disclosed herein. System 511 may include optical connector cable 560 with cable body 562 and distal connector 566. Guidewire 10 may be coupled to optical connector cable 560. Distal connector 566 may be a rotatable connector that allows guidewire 10 to rotate relative to optical connector cable 560.

Distal connector 566 may include body 580 with threaded end 580a. Collet 578 may be disposed within body 580. Collet nut 572 may be coupled to body 580, for example at end 580a. Connector 566 may also include a button ring 599, proximal body 568, housing 598 including button 597, a crimp sleeve 596, and a connector 592. Connector 592 may include ferrule 586. In some embodiments, connector 592 may be a SENKO 254 SERIES PREMIUM CONNECTOR BODY, 126 µm FERRULE. This is just an example.

In use, guidewire 10 may extend through collet nut 572, through retaining ring 576a, through collet 578, through a cap 576b, through first bearing 594a, through body 580, through second bearing 594b, and into ferrule 582. Ferrule 582 may extend into split sleeve 584. Tightening collet nut 572 onto body 580 may press collet 578 onto guidewire 10 and secure guidewire 10. Cable body 562 may include optical fiber 564, which extends through body 568, through housing 598, through crimp sleeve 596, and through connector 592 where fiber 564 may be secured to ferrule 586 (and secured thereto using a suitable bond such as an adhesive bond). Ferrule 586 may extend into split sleeve 584 so that fiber 564 can be positioned adjacent to fiber 24. Coupler 570 may be disposed within split sleeve 584 at a position between optical fiber 24 (of guidewire 10) and optical fiber 564. Coupler 570 may be similar in form and function to other couplers disclosed herein.

As indicated above, distal connector 566 may be a rotatable connector that allows guidewire 10 to rotate relative to connector cable 560. For example, distal connector 566 may include bearings 594a/594b that allows guidewire 10 to rotate relative to connector cable 560. Body 580 may include one or more projections 595. Projections 595 may be engaged when a button 599a on button ring 599 is depressed or otherwise deformed so as to grip body projections 595 (e.g., when button ring 599 is positioned over housing 598). This may include engaging button 597 on housing 598. Gripping projections 595 may allow collet nut 572 to be secured to body 580.

FIGS. 14-15 illustrate a portion of example medical device system 511' that may be similar in form and function to other systems disclosed herein. System 511', for example, is similar to system 511 except that distal connector 566' includes housing 598' that is shorter in length than housing 598. For example, housing 598' may have a length on the order of about 1 to 2 inches or so (e.g., about 1.5 inches).

The materials that can be used for the various components of guidewire 10 (and/or other guidewires disclosed herein) and the various tubular members disclosed herein may include those commonly associated with medical devices. For simplicity purposes, the following discussion makes reference to tubular member 12 and other components of guidewire 10. However, this is not intended to limit the devices and methods described herein, as the discussion may be applied to other similar tubular members and/or components of tubular members or devices disclosed herein.

Tubular member 12 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about –60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of tubular member 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into guidewire 10. For example, tubular member 12 or portions thereof may be made of a material that does not substantially distort the image and create substantial artifacts (i.e., gaps in the image). Certain ferromagnetic materials, for example, may not be suitable because they may create artifacts in an MRI image. Tubular member 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of tubular member 12 that may define a generally smooth outer surface for guidewire 10. In other embodiments, however, such a sheath or covering may be absent from a portion of all of guidewire 10, such that tubular member 12 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guidewire 10 (including, for example, the exterior surface of tubular member 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of tubular member 12, or other portions of guidewire 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Various embodiments of arrangements and configurations of slots are also contemplated that may be used in addition to what is described above or may be used in alternate embodiments. For simplicity purposes, the following disclosure makes reference to guidewire 10, slots 18, and tubular member 12. However, it can be appreciated that these variations may also be utilized for other slots and/or tubular members. In some embodiments, at least some, if not all of slots 18 are disposed at the same or a similar angle with respect to the longitudinal axis of tubular member 12. As shown, slots 18 can be disposed at an angle that is perpendicular, or substantially perpendicular, and/or can be characterized as being disposed in a plane that is normal to the longitudinal axis of tubular member 12. However, in other embodiments, slots 18 can be disposed at an angle that is not perpendicular, and/or can be characterized as being disposed in a plane that is not normal to the longitudinal axis of tubular member 12. Additionally, a group of one or more slots 18 may be disposed at different angles relative to another group of one or more slots 18. The distribution and/or configuration of slots 18 can also include, to the extent applicable, any of those disclosed in U.S. Pat. Publication No. US 2004/0181174, the entire disclosure of which is herein incorporated by reference.

Slots 18 may be provided to enhance the flexibility of tubular member 12 while still allowing for suitable torque transmission characteristics. Slots 18 may be formed such that one or more rings and/or tube segments interconnected by one or more segments and/or beams that are formed in tubular member 12, and such tube segments and beams may include portions of tubular member 12 that remain after slots 18 are formed in the body of tubular member 12. Such an interconnected structure may act to maintain a relatively high degree of torsional stiffness, while maintaining a desired level of lateral flexibility. In some embodiments, some adjacent slots 18 can be formed such that they include portions that overlap with each other about the circumference of tubular member 12. In other embodiments, some adjacent slots 18 can be disposed such that they do not necessarily overlap with each other, but are disposed in a pattern that provides the desired degree of lateral flexibility.

Additionally, slots 18 can be arranged along the length of, or about the circumference of, tubular member 12 to achieve desired properties. For example, adjacent slots 18, or groups of slots 18, can be arranged in a symmetrical pattern, such as being disposed essentially equally on opposite sides about the circumference of tubular member 12, or can be rotated by an angle relative to each other about the axis of tubular member 12. Additionally, adjacent slots 18, or groups of slots 18, may be equally spaced along the length of tubular member 12, or can be arranged in an increasing or decreasing density pattern, or can be arranged in a non-symmetric or irregular pattern. Other characteristics, such as slot size, slot shape, and/or slot angle with respect to the longitudinal axis of tubular member 12, can also be varied along the length of tubular member 12 in order to vary the flexibility or other properties. In other embodiments, moreover, it is contemplated that the portions of the tubular member, such as a proximal section, or a distal section, or the entire tubular member 12, may not include any such slots 18.

As suggested herein, slots 18 may be formed in groups of two, three, four, five, or more slots 18, which may be located at substantially the same location along the axis of tubular member 12. Alternatively, a single slot 18 may be disposed at some or all of these locations. Within the groups of slots 18, there may be included slots 18 that are equal in size (i.e., span the same circumferential distance around tubular member 12). In some of these as well as other embodiments, at least some slots 18 in a group are unequal in size (i.e., span a different circumferential distance around tubular member 12). Longitudinally adjacent groups of slots 18 may have the same or different configurations. For example, some embodiments of tubular member 12 include slots 18 that are equal in size in a first group and then unequally sized in an adjacent group. It can be appreciated that in groups that have two slots 18 that are equal in size and are symmetrically disposed around the tube circumference, the centroid of the pair of beams (i.e., the portion of tubular member 12 remaining after slots 18 are formed therein) is coincident with the central axis of tubular member 12. Conversely, in groups that have two slots 18 that are unequal in size and whose centroids are directly opposed on the tube circumference, the centroid of the pair of beams can be offset from the central axis of tubular member 12. Some embodiments of tubular member 12 include only slot groups with centroids that are coincident with the central axis of the tubular member 12, only slot groups with centroids that are offset from the central axis of tubular member 12, or slot groups with centroids that are coincident with the central axis of tubular member 12 in a first group and offset from the central axis of tubular member 12 in another group. The amount of offset may vary depending on the depth (or length) of slots 18 and can include other suitable distances.

Slots 18 can be formed by methods such as micromachining, saw-cutting (e.g., using a diamond grit embedded semiconductor dicing blade), electron discharge machining, grinding, milling, casting, molding, chemically etching or treating, or other known methods, and the like. In some such embodiments, the structure of the tubular member 12 is formed by cutting and/or removing portions of the tube to form slots 18. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 110 may include forming slots 18 tubular member 12 using these or other manufacturing steps.

In at least some embodiments, slots 18 may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow tubular member 12 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form tubular member 12 without being limited by a minimum cutting blade size. Consequently, tubular member 12 may be fabricated for use in neurological devices or other devices where a relatively small size may be desired.

U.S. Patent Application Publication No. US 2014/0058275 is herein incorporated by reference.

U.S. patent application Ser. No. 14/196,740 filed Mar. 4, 2014 is herein incorporated by reference.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device system for measuring blood pressure, the system comprising:
   a pressure sensing guidewire including a pressure sensor and a first optical fiber extending proximally from the pressure sensor;
   wherein the first optical fiber has a proximal end;
   an optical connector cable including a distal connector capable of being coupled to the guidewire;
   wherein the guidewire is rotatable relative to the optical connector cable while the guidewire is axially secured to the optical connector cable;
   wherein the optical connector cable includes a second optical fiber that is capable of optically communicating with the first optical fiber;
   wherein the second optical fiber has a distal end; and
   a cushioning member for cushioning the interface between the first optical fiber and the second optical fiber during rotation of the guidewire relative to the optical connector cable and during rotation of the first optical fiber relative to the second optical fiber, the cushioning member being disposed within the distal connector and disposed between the proximal end of the first optical fiber and the distal end of the second optical fiber, wherein the cushioning member includes a polymer disc and wherein the cushioning member is designed to prevent the proximal end of the first optical fiber from contacting the distal end of the second optical fiber.

2. The system of claim 1, wherein the cushioning member has an index of refraction that is the same as the index of refraction of the first optical fiber, the second optical fiber, or both.

3. The system of claim 1, wherein the cushioning member has a thickness of 25 to 400 microns.

4. The system of claim 1, wherein the optical connector cable includes a rotatable connector, wherein the rotatable connector includes a collet.

5. The system of claim 4, wherein the collet is coupled to a rotatable body having one or more projections formed thereon.

6. The system of claim 5, wherein the distal connector includes an outer deflectable member that is capable of engaging the one or more projections formed on the rotatable body.

7. The system of claim 1, wherein one or more bearings are disposed adjacent to the distal connector.

8. The system of claim 1, wherein the pressure sensing guidewire includes a tubular member having a plurality of slots formed therein.

9. The system of claim 8, wherein the number of slots per unit length varies along the tubular member.

10. The system of claim 9, wherein the tubular member includes a distal portion with a variable inner diameter.

11. A system for determining fractional flow reserve, the system comprising:
    a pressure sensing guidewire including an optical pressure sensor and a first optical fiber extending proximally from the optical pressure sensor;
    wherein the first optical fiber has a first index of refraction and has a proximal end;
    an optical connector cable including a rotatable distal connector capable of being rotatably coupled to the guidewire;
    a processing unit coupled to the optical connector cable;
    wherein the optical connector cable includes a second optical fiber that is capable of optically communicating with the first optical fiber;
    wherein the second optical fiber has a second index of refraction and has a distal end;
    a cushioning member disposed within the optical connector cable and disposed between the proximal end of the first optical fiber and the distal end of the second optical fiber, the cushioning member being designed to cushion the interface between the first optical fiber and the second optical fiber during rotation of the guidewire relative to the optical connector cable;
    wherein the cushioning member is designed to prevent the proximal end of the first optical fiber from contacting the distal end of the second optical fiber;
    wherein the cushioning member includes a polymer disc; and
    wherein the cushioning member has a third index of refraction that is the same as the first index of refraction, the second index of refraction, or both.

* * * * *